US006835755B1

(12) United States Patent
Meyer et al.

(10) Patent No.: US 6,835,755 B1
(45) Date of Patent: Dec. 28, 2004

(54) NAPHTHOQUINONE DERIVATIVES AND THEIR USE IN THE TREATMENT AND CONTROL OF TUBERCULOSIS

(75) Inventors: Jacobus Johannes Marion Meyer, Pretoria (ZA); Namrita Lall, Pretoria (ZA)

(73) Assignees: University of Pretoria, Pretoria (ZA); South African Medical Research Council, Parow (ZA)

( * ) Notice: Subject to any disclaimer, the term of this patent is extended or adjusted under 35 U.S.C. 154(b) by 0 days.

(21) Appl. No.: 09/926,807

(22) PCT Filed: May 22, 2000

(86) PCT No.: PCT/IB00/00837

§ 371 (c)(1), (2), (4) Date: Mar. 19, 2002

(87) PCT Pub. No.: WO01/00554

PCT Pub. Date: Jan. 4, 2001

(30) Foreign Application Priority Data

Jun. 24, 1999 (ZA) .............................................. 99/4176

(51) Int. Cl.[7] ................................................ A61K 31/12
(52) U.S. Cl. ....................................... 514/682; 514/924
(58) Field of Search ................................. 514/682, 924

(56) References Cited

U.S. PATENT DOCUMENTS 4,837,399 A * 6/1989 Baker et al. ................ 514/468

OTHER PUBLICATIONS

Vichkanova et al., "Search for antimicrobial drugs among quinones of plant orgin", Restit. Resur. (1979), 15(2), pp. 167–177, abstract enclosed.*

Evans et al., Plumbagin from Diospyros olen, MDPI, Apr. 16, 2004, Molecules 1999, 4, M93.

Osman et al., "Synthesis of Sulfanilamido–Naphthoquinones as Potential Antituberculous Agents", pp. 68–71, Jan. 1983, Journal of Pharmaceutical Sciences vol. 2, No. 1.

Adeniyi, B. A. et al: "Antibacterial activity of diospyrin, isodiospyrin and bisisodiospyrin from the root of Diospyros piscatoria (Gurke) (Ebenaceae)" Phytother. Res. (2000), 14 (2), 112–117, XP000978371—the whole document.

Khan M. R. et al: "Antibiotic Action of Constituents of Root Bark of Euclea–Natalensis." Pak J. Sci Ind Res, (1978 (RECD 1979)) 21 (5–6), 197–199, XP000978450—the whole document.

Khan, M. R. (1) Et Al: "Constituents of Diospyros Iolin, D. maritima and D. novoguinensis." Fitoterapia, (Apr., 1999) vol. 70, No. 2, pp. 194–196, XP000978591—the whole document.

Database Chemabs Online!, Chemical Abstracts Service, Columbus, Ohio, US; Vichkanova, S. A. et al: "Search for antimicrobial drugs among quinones of plant origin" retrieved from STN database accession No. 91:83030 XP002157353 abstract & RASTIT. Resur. (1979), 15(2), 167–77.

Roushdi I M, et al: "Synthesis of 1.4–naphthoquinones–4–aryl(Aroyl)hydrazone s of potential antimicrobial activity." Pharmazie, (17=976) 31 (12) 856–9., XP000971908 abstract.

Hazra Banasri et al: "In vitro antiplasmodial effects of diospyrin, a plant–derived naphthoquinoid, and a novel series of derivatives" Phytother. Res. (1995), 9(1), 72–4, XP000978372—the whole document.

Yardley, Vanessa et al: "In vitro activity of diospyrin and derivatives agianst Leishmania donovani, Trypanosoma cruzi and Trypanosoma brucei brucei" Phytother. Res. (1996), 10(7), 559–562, XP000978369—the whole document.

Hazra, Banasri et al: "Biological acitivity of diospyrin towards Ehrlich ascites carcinoma in Swiss A mice" Planta Med. (1984), 50(4), 295–7, XP000978377—the whole document.

Hazra, Banasri et al: "New diospyrin derivatives with improved tumor inhibitory activity towards Ehrlich ascites carcinoma" Med. Sci. Res. (1994), 22(5), 351–3, XP000978374—the whole document.

Oeriu I: "Relation between the chemical structure and the antitubercular effect of alpha–naphthoquinone derivatives substituted in 2 and 3 positions." Pharmazi, (May 1961) 16 266–72., XP000971910 table 5.

Oeriu I: "Zusammenhange zwischen der chemischen Struktur und der antituberkulosen Wirkung der in Stellung 2 und 3 substituieren Derivate des alpha–Naphthochinons" Pharmazi, DD, Veb Verlag Volk Und Gesundheit, Barlin, No. 16, 1961, pp. 320–327, XP002078405 ISSN: 0031-7144, table 8.

* cited by examiner

*Primary Examiner*—Kevin E. Weddington
(74) *Attorney, Agent, or Firm*—Nixon Peabody LLP; Donald R. Studebaker

(57) ABSTRACT

Naphthoquinone derivatives of Formula (1): wherein R, represents an OH group, methyl ether, ethyl ether or a similar ether, R1 represents a methyl, ethyl or similar aliphatic hydrocarbon derivative: R2 and R3 each independently represent hydrogen or a group selected from: (A), (B), or (C) wherein R5 represents an PH group, methyl ether, ethyl ether or a similar ether and R6 represents a methyl, ethyl or similar aliphatic hydrocarbon derivative: R4 represents hydrogen or a group selected from: (D), (E) or (F) wherein R7 represents an OH group, methyl ether, ethyl ether or a similar ether and R8 represents a methyl, ethyl or similar aliphatic hydrocarbon derivative: or pharmaceutically acceptable salts thereof, are useful for the treatment and/or control of a *tuberculosis* in a patient caused by *Mycobacterium tuberculosis.*

4 Claims, No Drawings

NAPHTHOQUINONE DERIVATIVES AND THEIR USE IN THE TREATMENT AND CONTROL OF TUBERCULOSIS

BACKGROUND OF THE INVENTION

THIS invention relates to the treatment and control of *tuberculosis* caused by *Mycobacterium tuberculosis* and in particular to the use of naphthoquinone derivatives in such treatment and control.

*Tuberculosis* (*TB*) remains a serious health problem in many regions of the world, especially in developing nations. It is a contagious disease and is becoming epidemic in some parts of the world. It is estimated that 30–60% of adults in developing countries are infected with *Mycobacterium tuberculosis*. Approximately 8–10 million individuals develop clinical *TB* and 3 million die of *TB* each year (WHO/IUATLD, 1989).

In South Africa, over 3 in every thousand people die of *TB*, the highest rate in the world, while one out of every 200 people suffers from active *tuberculosis*. *Tuberculosis* is the most commonly notified disease in South Africa and the fifth largest cause of death among the black population (South African *Tuberculosis* Association, 1998).

In the United States, the number of *TB* cases steadily decreased until 1986 when an increase was noted. Since then *TB* cases have continued to rise. Ten million individuals are infected in the U.S.A., with approximately 26000 new cases of active disease each year (National Jewish Medical and Research Center, 1994).

Individuals infected with Human Immunodeficiency Virus (HIV) are very susceptible to *tuberculosis* and often develop this disease before other manifestations of AIDS become apparent (Grange and Davey, 1990). Control of the *TB* epidemic linked with HIV infection will depend largely on the adequate treatment of *TB*, and possibly of effective chemoprophylaxis, not just for HIV-infected persons but for communities as well (WHO/IUATLD, 1989).

*TB* therapy has been revolutionized and the present treatment regimes for *TB* are based on multidrug therapy with usually 3 or 4 antituberculosis drugs. However, the problem of multidrug resistant *tubercle bacilli* is emerging for various drugs such as isoniazid, ethambutol, rifampicin and streptomycin, for example (Girling, 1989; Grange and Davey, 1990). Drug-resistant *TB* is very difficult to treat requiring greater numbers and varieties of medications for a longer period of treatment. The need for new antituberculosis agents is urgent due to the increasing resistance of *mycobacteria* to these classic antituberculosis drugs. A recent WHO report states that, globally, 2% of all cases of *tuberculosis* are multidrug resistant—by definition, resistance to rifampicin plus isoniazid (plus/minus other resistances). Such cases can be treated in the USA and other high resource regions but at a great cost (>US$ 250,000 per case!) and using very long courses of rather toxic drugs, thereby raising serious problems of compliance (WHO, 1997). South Africa is witnessing an explosion in the number of cases of drug-resistant *tuberculosis*. In some parts of South Africa, 1 in 10 cases of *TB* is resistant to treatment (New Scientist, March 1997). It is essential to have new antituberculosis agents, preferably those that can readily and simply be produced from some local source.

SUMMARY OF THE INVENTION

According to a first aspect of the invention there is provided a naphthoquinone derivative of Formula 1:

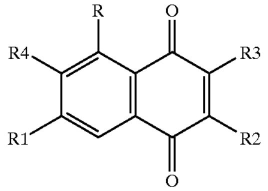

wherein,

R represents an OH group, methyl ether, ethyl ether or a similar ether;

R1 represents a methyl, ethyl or similar aliphatic hydrocarbon derivative;

R2 and R3 each independently represent hydrogen or a group selected from:

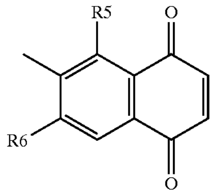
;
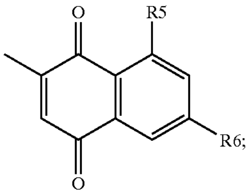
or
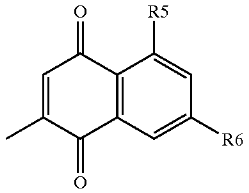

wherein R5 represents an OH group, methyl ether, ethyl ether or a similar ether and R6 represents a methyl, ethyl or similar aliphatic hydrocarbon derivative;

R4 represents hydrogen or a group selected from:

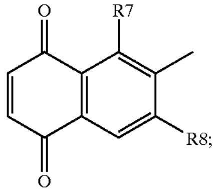
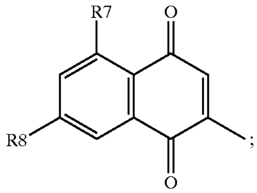
; or
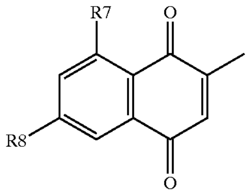

wherein R7 represents an OH group, methyl ether, ethyl ether or a similar ether and R8 represents a methyl, ethyl or similar aliphatic hydrocarbon derivative:

or pharmaceutically acceptable salts thereof, for use in a method of treating and/or controlling *tuberculosis* in a patient caused by *Mycobacterium tuberculosis*.

According to a second aspect of the invention there is provided the use of a naphthoquinone derivative having the Formula 1 as set out above in the manufacture of a medicament for use in a method of treating and/or controlling *tuberculosis* in a patient caused by *Mycobacterium tuberculosis.*

According to a third aspect of the invention there is provided a method of treating and/or controlling *tuberculosis* caused by *Mycobacterium tuberculosis* comprising administering to a patient in need thereof an effective amount of a naphthoquinone derivative having the Formula 1 as set out above.

The naphthoquinone derivative of Formula 1 is typically a compound of Formula 1a or Formula 1b:

Formula 1a

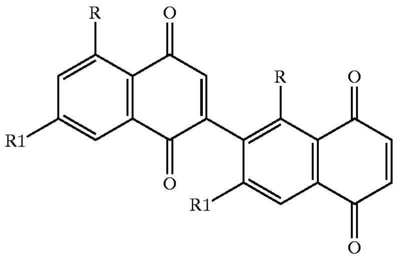

Formula 1b

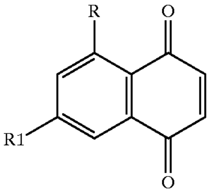

wherein R and R1 are as defined for Formula 1 above.

R in the compound of Formula 1a or 1b is preferably an OH group.

R1 in the compound of Formula 1a or 1b is preferably a $CH_3$ group.

In particular, the naphthoquinone derivative of Formula 1 is 5,5' dihydroxy 7,7' binaphthoquinone (diospyrin) or 5-hydroxy-7-methyl-1,4-naphtoquinone (methyljuglone).

DESCRIPTION OF PREFERRED EMBODIMENTS

The present invention is directed at the use of naphthoquinone derivatives in the treatment and/or control of *tuberculosis* caused by *Mycobacterium tuberculosis*. In particular, naphthoquinone derivatives of the general Formula 1

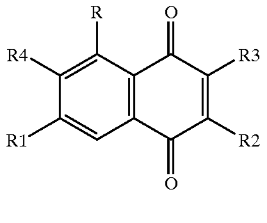

wherein,

R represents an OH group, methyl ether, ethyl ether or a similar ether;

R1 represents a methyl, ethyl or similar aliphatic hydrocarbon derivative;

R2 and R3 each independently represent hydrogen or a group selected from:

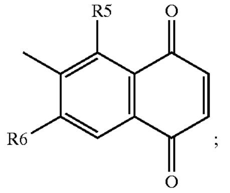

;

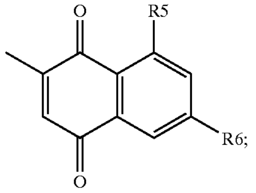

or

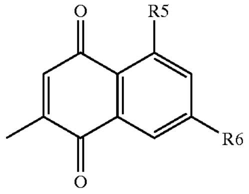

wherein R5 represents an OH group, methyl ether, ethyl ether or a similar ether and R6 represents a methyl, ethyl or similar aliphatic hydrocarbon derivative;

R4 represents hydrogen or a group selected from:

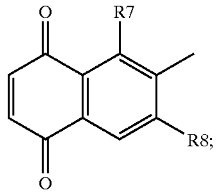

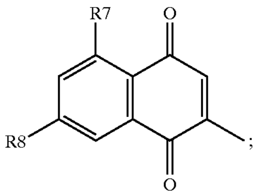

; or

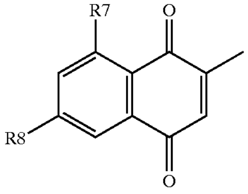

wherein R7 represents an OH group, methyl ether, ethyl ether or a similar ether and R8 represents a methyl, ethyl or similar aliphatic hydrocarbon derivative, have been found to be effective against *Mycobacterium tuberculosis.*

Particular naphthoquinone derivatives of Formula 1a and 1b have been found to be particularly effective:

Formula 1a

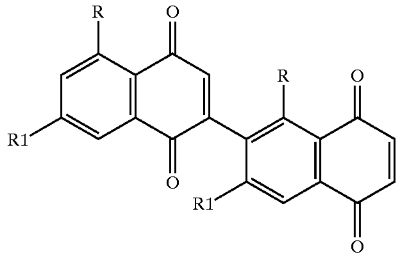

Formula 1b

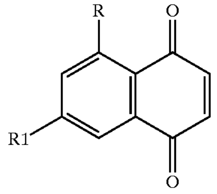

In particular diospyrin and methyljuglone, naphthoquinone derivatives of Formula 1a and Formula 1b, respectively, in which R is OH and R1 is a methyl group, have been found to inhibit several antibiotic resistant as well as antibiotic susceptible strains of *Mycobacterium tuberculosis*. Although diospyrin and methyljuglone are particularly preferred, naphthoquinone derivatives of Formula 1a and 1b in which R is a methyl ether, ethyl ether or similar ether and R1 is an ethyl or similar aliphatic hydrocarbon derivative are also provided.

An extensive research program was undertaken in order to identify antituberculosis agents that can readily and simply be produced from local resources.

Twenty South African medicinal plants used to treat pulmonary diseases were screened for activity against drug-resistant and sensitive strains of *M. tuberculosis*. A preliminary screening of acetone and water plant extracts, against a drug-sensitive strain of *M. tuberculosis*; H37Rv, was carried out by the agar plate method. Fourteen of the 20 acetone extracts showed inhibitory activity at a concentration of 0.5 mg/ml against this strain. Acetone as well as water extracts of *Cryptocarya latifolia, Euclea natalensis, Helichrysum melanacme, Nidorella anomala* and *Thymus vulgaris* inhibited the growth of *M. tuberculosis*. Given the activity of 14 acetone extracts at 0.5 mg/ml against the drug-sensitive strain by the agar plate method a further study was carried out employing the rapid radiometric method to confirm the inhibitory activity. These active acetone extracts were screened against the H37Rv strain as well as a strain resistant to the drugs, isoniazid and rifampicin. The minimal inhibitory concentration of *Croton pseudopulchellus, Ekebergia capensis, Euclea natalensis, Nidorella anomala* and *Polygala myrtifolia* was 0.1 mg/ml against the H37Rv strain by the radiometric method. Extracts of *Chenopodium ambrosioides, Ekebergia capensis, Euclea natalensis, Helichrysum melanacme, Nidorella anomala* and *Polygala myrtifolia* were active against the resistant strain at 0.1 mg/ml. Eight plants showed activity against both the strains at a concentration of 1.0 mg/ml.

The following procedure was developed by the applicant for the isolation of diospyrin and methyljuglone from *E. natalensis* and other species in this genus, as well as any other plants that may synthesise diospyrin or methyljuglone or other quinone derivatives.

1. Identification of Plant Species

Roots and the aerial plant parts of *E. natalensis* were collected near Durban and identified at the HGWJ Schweickerdt Herbarium of the University of Pretoria and also at the herbarium of the National Botanical Institute, Pretoria.

2. Extraction

Dried roots of *E. natalensis* were ground to a powdery form with a dry mill and extracted over 48 hours with acetone. The extract was filtered and concentrated to dryness at reduced pressure on a rotary evaporator.

3. Thin Layer Chromatography

A direct antibacterial bioassay (Dilika & Meyer 1996) on TLC-plates was employed to speedup the activity guided isolation of the antituberculosis compounds. *M. tuberculosis* cannot be tested in this way because of its very slow growth rate. The direct antibacterial bioassays of the acetone extract were done on TLC plates (Merck) developed with chloroform-hexane (1:1). After development, the TLC plates were dried and sprayed with a 24 hr old *Staphylococcus aureus* culture in nutrient broth. After 24 hr incubation, the plates were sprayed with an aqueous solution of 2 mg/ml p-iodonitrotetrazolium violet to visualise the bacterial cells. The plates were then reincubated at 37° C. for 2–3 hours.

Two zones of bacterial growth inhibition could be seen on TLC plates sprayed with *S. aureus*. Activity was more pronounced in the $R_f$ 10.30 zone (chloroform-hexane (1:1)) than in the $R_f$ 0.54 zone.

4. Column Chromatography

The crude extract of the plant was dried, its mass determined and resuspended in chloroform. Column chromatography was performed on silica gel 60 using chloroform as eluent. The antibacterial fractions collected were then subjected to a Sephadex LH-20 column chromatography using ethanol as eluent. The fractions collected were again tested for antibacterial activity on TLC to detect the fractions containing the active compounds of $R_f$ 0.30 and $R_f$ 10.54.

5. High Performance Liquid Chromatography

The compounds were further purified by HPLC utilising an analytical Phenomenex reverse phase 250×4.60 mm column, at a flow rate of 1.0 ml/min, oven temp. 40° C. and a wavelength of 206 nm. An ethanol-water (50:50) solution was employed as mobile phase. The pure compounds were once again subjected to a Sephadex LH-20 column chromatography and proved to be pure. The chemical structures were confirmed by $^1H$ and $^{13}C$ nmr and ms to be:

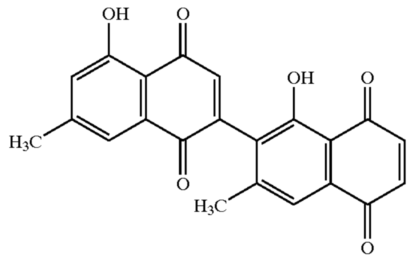

Diospyrin (5,5' dihydroxy 7,7' binaphthoquinone); $C_{22}H_{14}O_6$. Molecular weight: 374.35

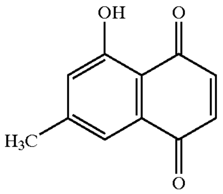

7-methyljuglone (5-hydroxy-7-methyl-1,4-naphtoquinone); $C_{11}H_8O_3$ Molecular weight: 188.19

The effect of diospyrin and methyljuglone on the growth of the sensitive strain (H37Rv) and resistant strains of *Mycobacterium tuberculosis* as determined by the radiometric method are set out in Table 1 and Table 2.

TABLE 1

Effect of diospyrin on the growth of the sensitive strain (H37Rv) and resistant strains of *Mycobacterium tuberculosis* as determined by the radiometric method.

| *Mycobacterium tuberculosis* strains | MIC (mg/ml) | ΔGI[a] values of plant extracts (mg/ml) | ΔGI values of the control vial (mg/ml) |
|---|---|---|---|
| H37 sensitive strain | 0.1 | −1 ± 1.41 | 20 ± 4.24 |
| 2 drug resistant strain (res. to Isoniazid and rifampicin). | 0.1 | 3.5 ± 0.70 | 25 ± 7.07 |
| 3 drug resistant strain (res. to streptomycin, isoniazid and ethambutol). | 0.1 | 4 ± 2.12 | 29 ± 1.41 |
| 4 drug resistant strain (res. to streptomycin, isoniazid, rifampicin and ethambutol). | 0.1 | 5 ± 2.82 | 25 ± 2.82 |
| 5 drug resistant strain (res to isoniazid, streptomycin, rifampicin, thiacetazone and cyclocerine). | 0.1 | 10 ± 1.41 | 22.5 ± 3.53 |
| 6 drug resistant strain (res. to | 0.1 | 9 ± 2.82 | 30 ± 1.0 |

TABLE 1-continued

Effect of diospyrin on the growth of the sensitive strain (H37Rv) and resistant strains of *Mycobacterium tuberculosis* as determined by the radiometric method.

| *Mycobacterium tuberculosis* strains | MIC (mg/ml) | ΔGI[a] values of plant extracts (mg/ml) | ΔGI values of the control vial (mg/ml) |
|---|---|---|---|
| isoniazid, rifampicin, ethionamide, terizidone, thiacetazone and ofloxacin). | | | |
| 7 drug resistant strain (res to isoniazid, streptomycin, ethambutol, kanamycin, rifampicin, and ethionamide) | 0.1 | 13.5 ± 3.2 | 28 ± 3.1 |

[a]ΔGI values are means ± s.d.

TABLE 2

Effect of 7-methyljuglone as a single agent and in combination with diospyrin on the growth of the sensitive strain (H37Rv) and resistant strains of *Mycobacterium tuberculosis* as determined by the radiometric method.

| *Mycobacterium tuberculosis* strains | Lab reference no. | Compound(s) | MIC[a] (μg/ml) | ΔGI[b] values of plant extracts | ΔGI values of the control vial |
|---|---|---|---|---|---|
| H37Rv sensitive strain | ATCC27294 | 7-methyljuglone | 50 | 0 ± 1 | 15 ± 3.78 |
| Two drug (isoniazid and rifampicin) resistant strain | CCKO28469V | 7-methyljuglone | 50 | 0 ± 0 | 30 ± 4.94 |
| H37Rv sensitive strain | ATCC27294 | Diospyrin + 7-methyljuglone | 10 | 3 ± 1 | 15 ± 3.78 |
| Two drug (Isoniazid and rifampicin resistant strain) | CCKO28469V | Diospyrin + 7-methyljuglone | 10 | 3.33 ± 3.05 | 30 ± 4.94 |

[a]Minimal inhibitory concentration
[b]ΔGI values are means ± s.d.

The results show that diospyrin and methyljuglone control the *Mycobacterium tuberculosis* bacterium effectively. Oral administration of diospyrin or methyljuglone in an appropriate pharmaceutical composition with suitable diluents and carriers will typically be used to treat or control *tuberculosis*. This will be by way of tablet, liquid or similar oral dosage form, as diospyrin and methyljuglone are readily absorbed intestinally.

However, it is believed that diospyrin or methyljuglone administered intravenously or intramuscularly will also be absorbed effectively through blood vessels and the blood stream of a patient. Transdermal administration, via a plaster or similar transdermal administration vehicle, is also a possibility.

A combination treatment of diospyrin and methyljuglone, which may be more effective than singular treatments of the two naphthoquinones, is also envisaged.

The applicant believes that it may be possible to increase the concentration of diospyrin, methyljuglone and other quinones in *E. natalensis* or similar species by phytoalexic stimulation or by the biotechnological manipulation of tissue cultures and/or intact plants.

Quinones are generally synthesised from catechol (1,2-quinones) or hydroquinone (1,4-quinones) by mild oxidation.

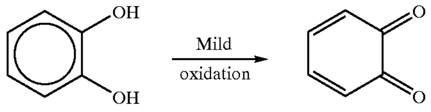

Catechol

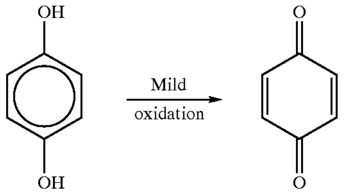

Hydroquinone

As far as the applicant has been able to establish, diospyrin has been synthesised once in a laboratory (Yoshida, M and Mori. K. 2000. European Journal of Organic Chemistry pages 1313–1317). However, similar binapthoquinones can also be synthesised by the reaction of plumbagin (94 mg in methanol, 10 ml) and its hydroquinone (190 mg in methanol, 14 ml), buffered in phosphate to pH 6.8 at 30° C. (Sankaram et al. 1975; Kumari et al. 1982).

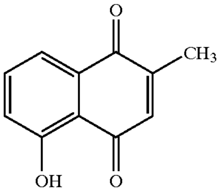

Plumbagin

It is believed that diospyrin, methyljuglone and related naphthoquinone derivatives are viable alternatives to conventional drugs in the treatment and control of *tuberculosis* in humans.

What is claimed is:

1. A method of treating and/or controlling *tuberculosis* caused by *Mycobacterium tuberculosis* comprising:

administering to a patient in need thereof a therapeutically effective amount of a naphthoquinone derivative having the Formula 1:

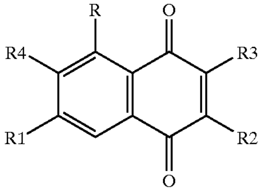

wherein,

R represents an OH group;

R1 represents a methyl group;

R2 and R3 each independently represent hydrogen or a group selected from:

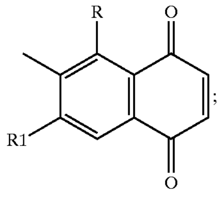

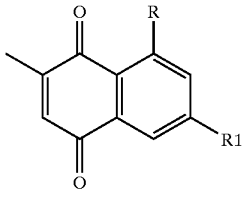

; or

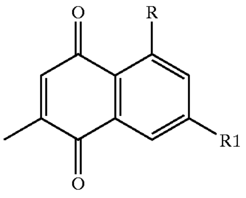

wherein R and R1 are as defined above; and

R4 represents hydrogen or a group selected from:

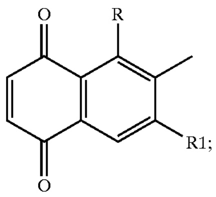

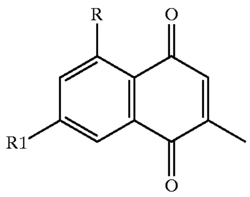

; or

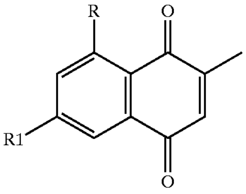

wherein R and R1 are as defined above, or pharmaceutically acceptable salts thereof.

2. A method of treating and/or controlling *tuberculosis* caused by *Mycobacterium tuberculosis* comprising:

administering to a patient in need thereof a therapeutically effective amount of a naphthoquinone derivative having the Formula 1:

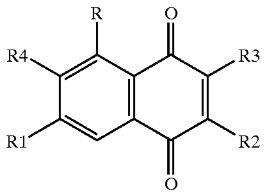

wherein,

R represents an OH group:

R1 represents a methyl group,

R2 and R3 each independently represent hydrogen or a group selected from:

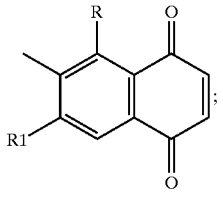

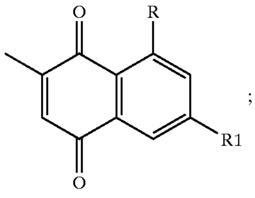

; or

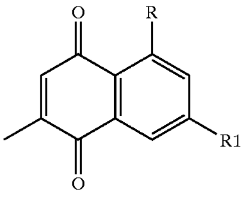

wherein R and R1 are as defined above; and

R4 represents hydrogen or a group selected from:

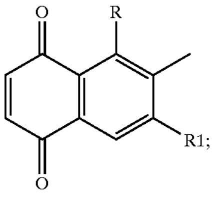

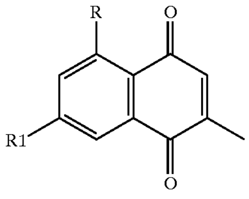

; or

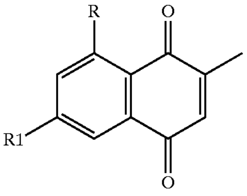

wherein R and R1 are as defined above, and wherein the naphthoquinone derivative of Formula 1 is a compound of Formula 1a or Formula 1b:

Formula 1a

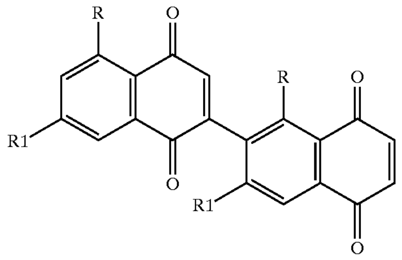

Formula 1b

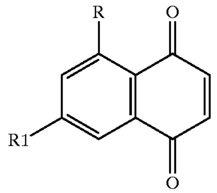

or pharmaceutically acceptable salts thereof.

3. A method according to claim 1 wherein the naphthoquinone derivative of Formula 1 is 5,5' dihydroxy 7,7' binaphthoquinone (diospyrin) or 5-hydroxy-7-methyl-1,4-naphtoquinone (7-methyljuglone), or a mixture thereof.

4. A method according to claim 1 wherein the naphthoquinone derivative of Formula 1 is administered orally, intravenously, intramuscularly or transdermally.

* * * * *